(12) United States Patent
Min

(10) Patent No.: US 8,211,049 B2
(45) Date of Patent: Jul. 3, 2012

(54) BLOOD PROCESSING SYSTEM FOR SINGLE OR DOUBLE ACCESS DRAW AND RETURN

(75) Inventor: Kyungyoon Min, Kildeer, IL (US)

(73) Assignee: Fenwal, Inc., Lake Zurich, IL (US)

( * ) Notice: Subject to any disclaimer, the term of this patent is extended or adjusted under 35 U.S.C. 154(b) by 439 days.

(21) Appl. No.: 12/392,193

(22) Filed: Feb. 25, 2009

(65) Prior Publication Data

US 2010/0217174 A1 Aug. 26, 2010

Related U.S. Application Data

(60) Provisional application No. 61/031,584, filed on Feb. 26, 2008.

(51) Int. Cl.
*A61M 37/00* (2006.01)
*A61M 1/00* (2006.01)

(52) U.S. Cl. ............... 604/6.01; 604/6.05; 604/6.06; 604/6.1; 422/44

(58) Field of Classification Search ............. 604/6.01, 604/6.05, 6.06; 422/44
See application file for complete search history.

(56) References Cited

U.S. PATENT DOCUMENTS

| | | | | |
|---|---|---|---|---|
| 6,027,441 A | * | 2/2000 | Cantu et al. | 494/37 |
| 7,704,454 B1 | * | 4/2010 | Langley et al. | 422/44 |
| 2002/0099319 A1 | * | 7/2002 | Saito et al. | 604/6.04 |
| 2003/0211927 A1 | * | 11/2003 | Cantu et al. | 494/3 |
| 2004/0147865 A1 | * | 7/2004 | Cianci et al. | 604/6.01 |
| 2005/0124927 A1 | * | 6/2005 | Smith et al. | 604/6.03 |
| 2009/0043237 A1 | * | 2/2009 | Langley et al. | 604/6.02 |
| 2009/0129976 A1 | * | 5/2009 | Hoshino et al. | 422/44 |

OTHER PUBLICATIONS

Print out from http://www.jnj.com/connect/news/al1/20090323_094500; "U.S. FDA Approves New Therakos Cellex Photopheresis System" news release dated Mar. 23, 2010.

* cited by examiner

*Primary Examiner* — Leslie Deak
*Assistant Examiner* — Adam Marcetich
(74) *Attorney, Agent, or Firm* — Cook Alex Ltd.

(57) ABSTRACT

A blood processing system is disclosed which is adapted for single or double access draw and return. The blood processing system includes a blood processor for separating blood (or blood components) into one or more components or other components. In one embodiment the blood processor includes an inlet for receiving blood from blood source and an outlet for returning at least one blood component to the source. The processing system includes a first flow path in communication with the inlet, a second flow path in communication with the outlet, a third flow path in communication with a second flow path at two spaced apart locations, a reservoir communicates with the third flow path between the two spaced apart locations, and a flow communication site associated with the second flow path downstream of the spaced apart locations which communication site is adapted to permit communication with the first flow path.

18 Claims, 6 Drawing Sheets

BLOOD PROCESSING SYSTEM FOR SINGLE OR DOUBLE ACCESS DRAW AND RETURN

The present application claims the benefit of prior Provisional Application Ser. No. 61/031,584, filed Feb. 26, 2008 and entitled "Systems And Methods Allowing Single Needle And Double Needle Apheresis", which is hereby incorporated by reference in its entirety.

The present invention relates generally to blood apheresis and more specifically to systems and methods for carrying out apheresis.

Apheresis generally refers to the separation of blood into one or more component parts, such as red cells, plasma, platelets and leukocytes. Apheresis may be carried out for separating and collecting one or more components from healthy donors for later administration to patients requiring that particular blood component. For example, red blood cells may be collected from healthy donors for use in critical care environments involving patients who have suffered significant blood loss. Platelets may be collected from healthy donors for later administration to patients undergoing chemotherapy treatment for cancer. Similarly, plasma may be collected from healthy donors for a later replacement procedure in patients suffering from immunodisorders. In addition, apheresis may be carried out for therapeutic purposes, i.e., for removing blood components from a patient as part of the treatment regimen for that patient.

There are a number of apheresis systems commercially available, including the CS 3000®, Amicus® and Alyx® apheresis systems from Fenwal Corporation of Lake Zurich, Ill. Apheresis systems are also available from Gambro BCT of Lakewood, Colo. or Haemonetics Corp. of Braintree, Mass. While these apheresis systems may use different technology, a common feature is the use of a disposable tubing kit, through which the blood flows and is processed, and a durable, reusable hardware device that cooperates with the tubing kit to control flow therethrough and processing of blood components therewithin.

Disposable tubing kits for apheresis typically are commonly found in two different forms. Specifically, apheresis tubing kits are generally available as single access or single needle kits or as double access or double needle kits. While access to the vascular system is normally via needle(s) inserted transcutaneously, other access devices such as needleless connectors also may be used. With a single access tubing or flow kit, blood is withdrawn from the source, i.e., donor or patient or other source, and returned to the source through a single needle or single access site. This provides the advantage of only making a single puncture or access into the vascular system of a donor or patient, but can in certain circumstances prolong the procedure time because fluid must be alternatively withdrawn and returned through the same access site. Double access or double needle apheresis flow kits or tubing sets allow blood to be withdrawn through one access site or needle and returned through a second access site needle, thereby allowing essentially continuous and simultaneous withdrawal and return, potentially reducing procedure time, but also requiring two separate access sites or punctures, which can be inconvenient and uncomfortable for the donor or patient, and can place extra stress on the vascular system.

SUMMARY

As described herein, a blood processing system is described which is adapted for either single or double access draw and return. In one embodiment, the blood processing system includes a blood processor for separating blood into one or more components. The blood processor includes an inlet for receiving blood from a blood source and an outlet for returning at least one blood component to the source. The system includes a first flow path in communication with the processor inlet and a second flow path in communication with the processor outlet. The system further includes a third flow path in communication with the second flow path at two spaced apart locations. A reservoir is also provided which is in fluid communication with a third flow path between the two spaced apart locations. In addition, a flow communication site is associated with a second flow path downstream of the spaced apart locations, which communication site is adapted to permit communication with the first flow path.

As a consequence of this arrangement, as described more fully below, the user may employ the same blood processing system for either a single or double needle or access site apheresis procedure without having to maintain separate inventories of both single needle tubing kits and double needle access site tubing kits. For convenience, references hereinafter to "single needle" or "double needle" will be understood to include a single access site or dual access site, so as not to be limited to needle access, unless clearly indicated otherwise.

DESCRIPTION OF THE DRAWINGS

In FIG. 1 the fluid flow system is configured for double needle collection and draw procedure;

DETAILED DESCRIPTION

Figure 1:
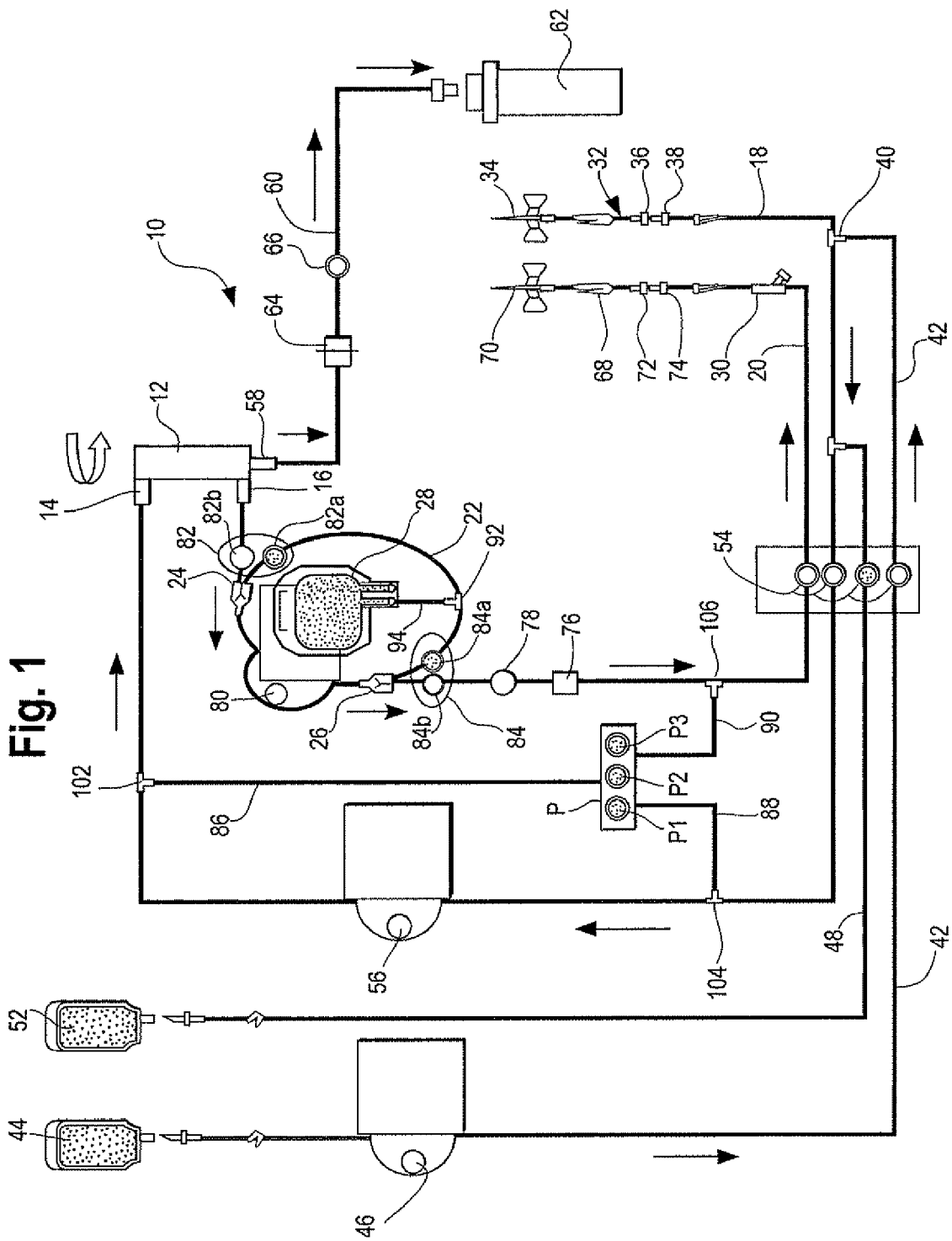
FIG. 1 is a diagrammatic view of an exemplary apheresis system for collecting plasma from whole blood received from a donor or patient or other blood source.

FIG. 1 illustrates a blood processing system for carrying out a plasma collection procedure. Of course, the subject matter described herein is not limited to a plasma collection procedure, and may be used in other procedures for collecting or withdrawing other blood components (such as red cells or platelets) from a donor, patient or other blood source, such as a container of pre-collected blood. Illustrated diagrammatically for purposes of description, the present subject matter would, in its preferred form, comprise a pre-assembled and pre-sterilized disposable tubing system through which the fluid to be processed, which is principally blood, would flow. As used herein, "blood" is comprehensive and includes whole blood in the condition withdrawn from a donor or a patient or including other fluids, such as anticoagulant, blood component preservatives or saline, or blood components that have been previously processed or selected. Such a disposable tubing system is intended to be employed in combination with a durable, reusable hardware system which includes associated pumps, sensors and the like for controlling blood flow and processing through the disposable system. Such systems are commonplace in the current apheresis marketplace. For example, such apheresis systems include the CS 3000°, and the Amicus® and Alyx® apheresis systems available from Fenwal Corporation of Lake Zurich, Ill., examples of which may be found in one or more of U.S. Pat. Nos. 4,526,515; 5,427,509; 5,738,792, 6,800,054 and 5,194,145, all of which are incorporated by reference herein.

More specifically, FIG. 1 depicts an apheresis system generally designated 10. The apheresis system includes a blood processor 12 for separating blood or blood components into one or more components or sub-components, such as plasma, platelets and red cells. The blood processor may operate on any suitable separation principle, such as centrifugation as in the Fenwal CS 3000, Amicus and Alyx systems, spinning membrane, and in the Fenwal Autopheresis C system or others which are well known in the field of apheresis. The blood processor includes an inlet 14 for receiving blood from a blood source (not shown) and an outlet 16 for returning one or more blood components to the blood source. The system further includes a first flow path 18 for flowing blood from a donor, patient, or other blood source to the inlet 14 of the blood processor 12. A second flow path 20 is provided, which is in communication with the outlet 16 of the blood processor 12 for returning one or more blood components to the donor or patient or other source. The illustrated system further includes a third flow path 22, which communicates with the second flow path at two spaced apart locations 24 and 26. A fluid reservoir 28, for example in the form of a blood bag, is in fluid communication with the third flow path between the first and second locations. As explained in more detail herein the reservoir 28 has multiple uses. It may receive excess priming liquid when the flow system is being initiated, and function as what is sometimes called a "waste" container. It may also function as a temporary reservoir for blood components separated by the processor 12 in a single needle procedure.

The second flow path 20, for returning one or more blood components to the blood source, includes a flow communication site 30 for optional communication with the first flow path 18 when it is desired to employ the system as a single needle draw and return system. The first flow path 18 does not communicate directly with the second flow path in the situation where it is desired to use the system as a double needle or access system. In the double needle or access arrangement, the first flow path 18 includes a separate access device or needle for drawing blood from the source.

Turning now to a more detailed description of the illustrated system 10. First flow path 18, for withdrawing blood from a blood source and communicating it to the processor 12, terminates in an optional access site. Specifically, as shown in the illustrated embodiment in FIG. 1, flow path 18 terminates in a removable needle or access device segment 32. The access device segment, as illustrated, has a needle 34 at one end for accessing the vessel of a patient or donor or for accessing another blood source such as a bag of pre-collected blood. For accessing a bag of pre-collected blood, the needle may be replaced with a needless connector, spike or piercing member of the types commonly known and used in the medical industry. The other end of the illustrated needle or access device segment 32 terminates in a fitting 36 for a removable connection to a mating fitting 38 so as to allow optional removal of the needle segment 32, for example, when it is desired to use the system as a single needle system.

The first flow path 18, as with the other flow paths described herein, may be of any suitable shape or form. Typically it may be made up of single or multiple lengths of medical grade tubing which convey blood or blood components to the inlet 14 of the blood processor 12. Alternatively, the first flow path 18 (and others described) could be defined in a rigid flow control cassette such as the cassettes used in the Fenwal Amicus and Alyx processing systems as illustrated and incorporated by reference in certain of the above-identified patents.

Following the first flow path 18 downstream from the needle segment 32, the flow path may include a first coupling or access site 40 for the addition of anticoagulant to blood withdrawn from a donor, patient or other blood source. The access site communicates, via the flow path 42 with a container or source of anticoagulant 44.

For metering the anticoagulant flow into the first flow path 18 (the blood inlet flow line), an anticoagulant pump 46 is operatively associated with the flow path 42. The anticoagulant pump may be a typical peristaltic pump of the type routinely found in apheresis systems or a pnuematically controlled diaphragm pump as found for example in the Fenwal Alyx® apheresis system. Other types of pumps may also be used to meter the flow of anticoagulant. The anticoagulant flow path may also have an internal flow of restriction for limiting the flow of anticoagulant in the case of a pump misassembly or misoperation. One such internal flow restriction is illustrated in U.S. Pat. No. 6,565,806, incorporated by reference herein.

For system priming as well as for the potential addition of saline to the blood process, a saline flow path 48 communicates between access site 50 in the first flow path 18 and a saline solution container or source 52. Further downstream, the first or blood inlet flow path 18 flows through one of an array of valves 54 or clamps for controlling flow through the first flow path. To control or meter the flow rate of whole blood from the blood source into the blood processor 12, a whole blood pump 56 is also cooperatively associated with the first flow path 18 and may be any of the variety of types of pumps mentioned above or others well known in the medical fluid processing field.

The first flow path 18, as explained earlier, communicates with the inlet 14 of the blood processor 12. As explained briefly earlier, the blood processor 12 may be any suitable device for separating one or more blood components from the whole blood received from the blood source. It may, for example, include a centrifugal chamber, a rotating membrane, a static membrane, or any other separation technology for separating one or more blood components from the whole blood. Examples of various processors may be found in the above cited patents. For blood components to be removed for later use or processing, the processor includes an outlet 58 that communicates, via flow path 60, with a storage container 62. As illustrated, the blood component to be separated and saved for later administration or processing is plasma, although the present subject matter is not limited to any particular blood component that is separated from the whole blood. In a conventional manner, the system 10 may include a sensor 64 in the flow path 60, as well as a clamp or valve 66 for opening, closing and/or proportionally controlling the flow through the flow path 60. Sensor 64 may function as a hemolysis sensor in certain applications, such as where the blood component removed from port 58 is plasma. Alternatively, sensor 64 may function as a hematocrit sensor in applications where the blood component removed from outlet 58 is red cells.

For returning separated blood components to the donor, patient or other blood source, the second fluid flow path 20 communicates from an outlet 16 of the processor to a distal needle or access device segment 68. The needle or access device segment may be removable or may be a continuous fixed portion of the flow path 20, terminating in a needle or other access device for accessing the vascular system of a patient or donor, or for accessing another blood source. As illustrated, the proximal end of the needle segment 68 terminates in a fitting 72 for removable attachment to filling 74, allowing the needle or access device segment 68 to be optionally removed. As pointed out above, however, the fittings 72 and 74 are not required, and the needle or access device segment may be a permanent part of the second flow path 20.

As noted earlier, a flow communication site 30 is provided in the second flow path 20 proximal or spaced from the needle or access device 70. The flow communication site 30 may be of any suitable configuration for attachment of the first or whole blood flow path 18. For example, the flow communication site 30 may comprise what is commonly referred to as a V-site or Y-site, wherein one of the flow branches of the site has a piercable or movable septum or other needle or needle-less connection site that is adapted for attachment, for example, to fitting 38 (such as a luer fitting) of the whole blood flow path. When fitting 38 is attached to the flow communication site 30, and valve 54 on the second flow path 20 is closed, the blood flow into needle 70 from the blood source is diverted into the first or whole blood inlet flow path 18. In other words, when fitting 38 is attached to the flow communication site 30, the system is in a single needle configuration, where blood is removed or drawn from the patient, donor or other blood source through access member or needle 70 and flows into the flow path 18 (due to closing of valve 54 on flowpath 20), to the processor 12 via pump 56, removed from the processor through outlet 16 and returned to the patient or donor through the flow path 20 and the same access device or needle 70—thus functioning as a fully single access device or needle system.

For secure attachment in the single access mode, the flow communication site 30 and fitting 38 may have a cooperating thread, lure lock or other connection arrangement for secure attachment of fitting 38 to the flow communication site 30. Upstream of the clamps 54, the second or return flow path 20 includes a conventional air detector 76 and filter 78, such as a micro-aggregate filter, for filtering blood components being returned to the donor. The return filter may be an aggregate filter or other suitable filter for removing any clots or undesired materials from the blood components being returned to the blood source. For metering or controlling the flow rate of blood components removed from the blood processor 12, a flow control pump 80, such as a peristaltic or diaphragm pump, may be cooperatively associated with the second or return flow path 20

As described earlier, a third flow path 22 communicates between spaced apart sites or locations 24 and 26 in the flow path 20. As a consequence, the third flow path 22 and the portion of flow path 20 located between the communication sites 24 and 26 together form a flow loop that may be controlled by activation of flow control clamps or valves 82a, 82b and 84a, 84b of valve arrays 82 and 84. To temporarily receive or hold separated blood components, the fluid reservoir 28 communicates with the third flow path 22 at access site 92 located between communication sites 24 and 26. As illustrated in FIG. 1, the reservoir is shown as a flexible blood bag, but any other suitable container rigid or flexible may be employed as the reservoir 28. As illustrated, the blood bag communicates with the flow path 22 via a short tubing segment 94.

For enhanced safety and/or operational benefits, fluid pressures in the system may be sensed by sensors in pressure sensor array P. Flow path 86 communicates between the first or whole blood flow path 18 at connector 102 and pressure sensor P2 for sensing pressure in the first flow path. The pressure in the first flow path is particularly useful to enhance the control or efficiency of separation in the blood processor 12. For example, where the blood processor 12 employs a membrane for separation, information about the pressure in the whole blood or first flow path may be employed to permit controlling of the transmembrane pressure within the processor for enhancing separation efficiency.

Pressure sensor P1 communicates with blood inlet or draw flow path 18 via flow path 88 and connector 104. P1 may be used to sense low flow pressures due to inflow obstructions such as vein obstructions or collapse in a donor/patient.

Pressure sensor P3 communicates with return line 20 via flow 90 and connector 106 to sense pressure of fluid in the return line. This allows sensing of excessive return pressures for donor safety purposes, as well as increased pressures due to obstruction in the return flow path.

The sensors P1, P2 and P3 are, in well known manner, operatively connected to a controller, e.g., a programmable controller, for controlling associated pumps and valves in response to the pressures detected in various flow paths. Further, although illustrated as an array of pressure sensors, each sensor may be separately directly associated with the respective flow path in which pressure is being sensed, and the illustrated embodiment is for purposes of description and not limitation. Also, it may be desirable in some circumstances to use fewer or more pressure sensors.

Figure 7:
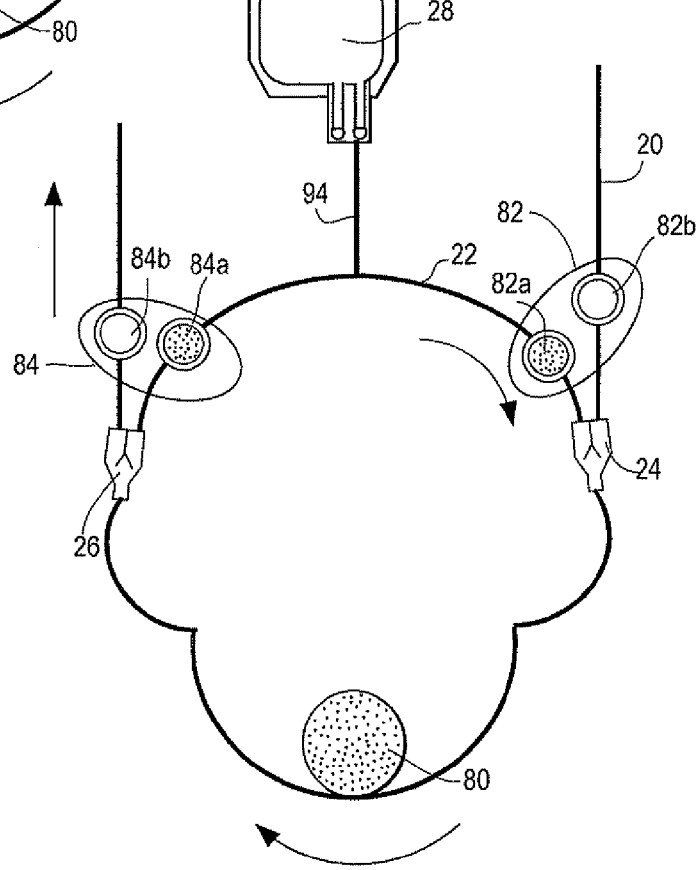
FIG. 7 illustrates a portion of the system of FIG. 1 when configured as a double needle system.

When the system of FIG. 1 is operated in the double or dual needle or access configuration, blood is drawn from the source, through needle 34 and into flow path 18 through which it flows, past open valve 54 and via pump 56, to the blood processor 12. Separated blood components to be returned to the blood source are removed from the blood processor at outlet 16 and flow through the second or return flow path 20, and are returned to the blood source through the needle or other access device 70. In this (dual needle) configuration, the first fluid flow path 18 is separate from and is not connected directly to the return flow path 20, so that blood is withdrawn from the blood source and returned to the blood source through separate flow paths/access sites. Further, in the dual needle or access device configuration, the valve arrays 82 and 84 are controlled so that blood components removed from the blood processor 12 flow essentially only through flow path 20, bypassing the third flow path 22. More specifically, in the dual needle arrangement, the valves 82a, 82b and 84a, 84b of arrays 82 and 84 are controlled to direct the flow of separated blood components via pump 80 through path 20 and to block flow path 22. In other words, valves 82a and 84a are closed and valves 82b and 84b are open, allowing blood components to flow from the blood processor 12 through the second or return flow path 20 and to the blood source through the needle or access device 70, and blocking flow through the third flow path 22. This arrangement is further depicted in FIG. 7 which shows only a portion of the overall blood processing system.

Figure 2:
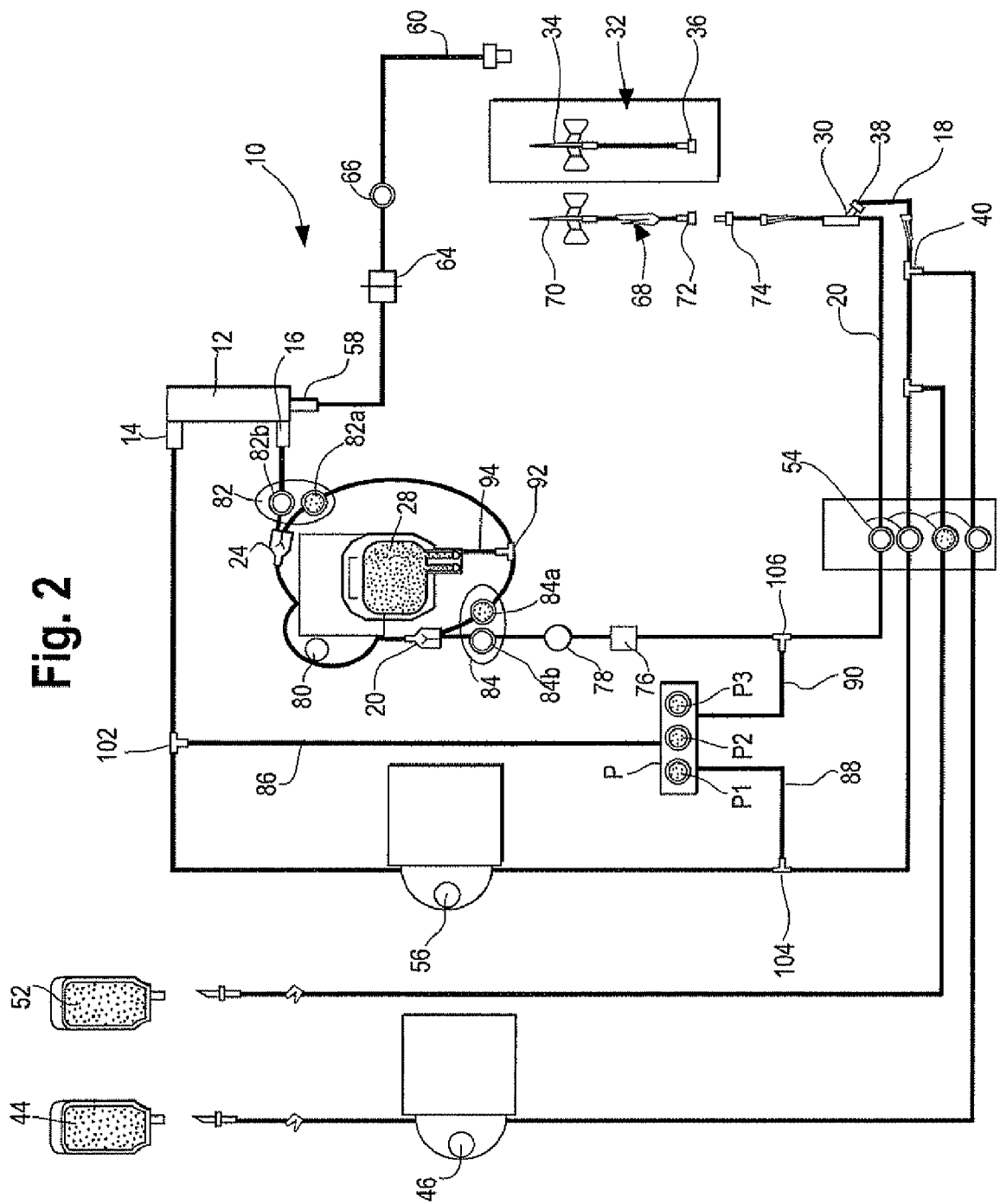
FIG. 2 illustrates the system of FIG. 1 configured as a single needle system.

FIG. 2 illustrates the blood processing system of FIG. 1 when it is configured for a single access device or single needle operation. In that configuration it may be seen that the needle or access device segment 32 has been separated and removed from the first or inlet flow path 18, and connector 38 of the inlet flow path 18 has been joined with the flow communication site 30 located in the second or return flow path 20.

While this description shows removable connections between connector 38 and flow communication site 30, the system may be constructed so that there is a permanent fluid junction between flow paths 18 and 20, and flow through the junction is controlled by valves or similar devices in order to maintain flow separation between flow paths 18 and 20 or to allow flow therebetween as desired for single or double access device processing. In any event, as illustrated in FIG. 2, the first or whole blood flow path 18 is shown in direct flow communication with the communication site 30.

Figure 3:
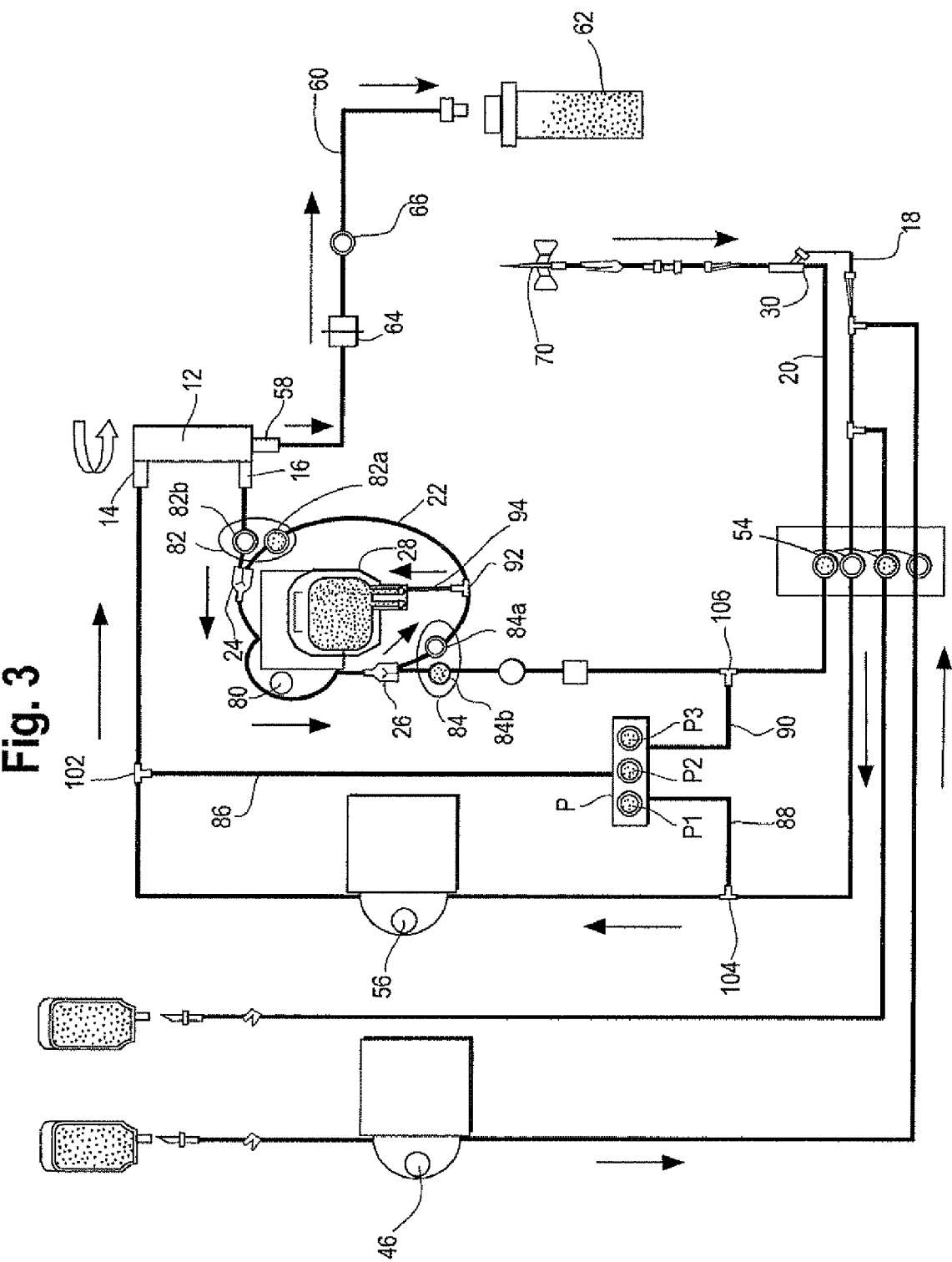
FIG. 3 is a diagrammatic view showing flow through the system of FIG. 2 in a draw cycle.
Figure 4:
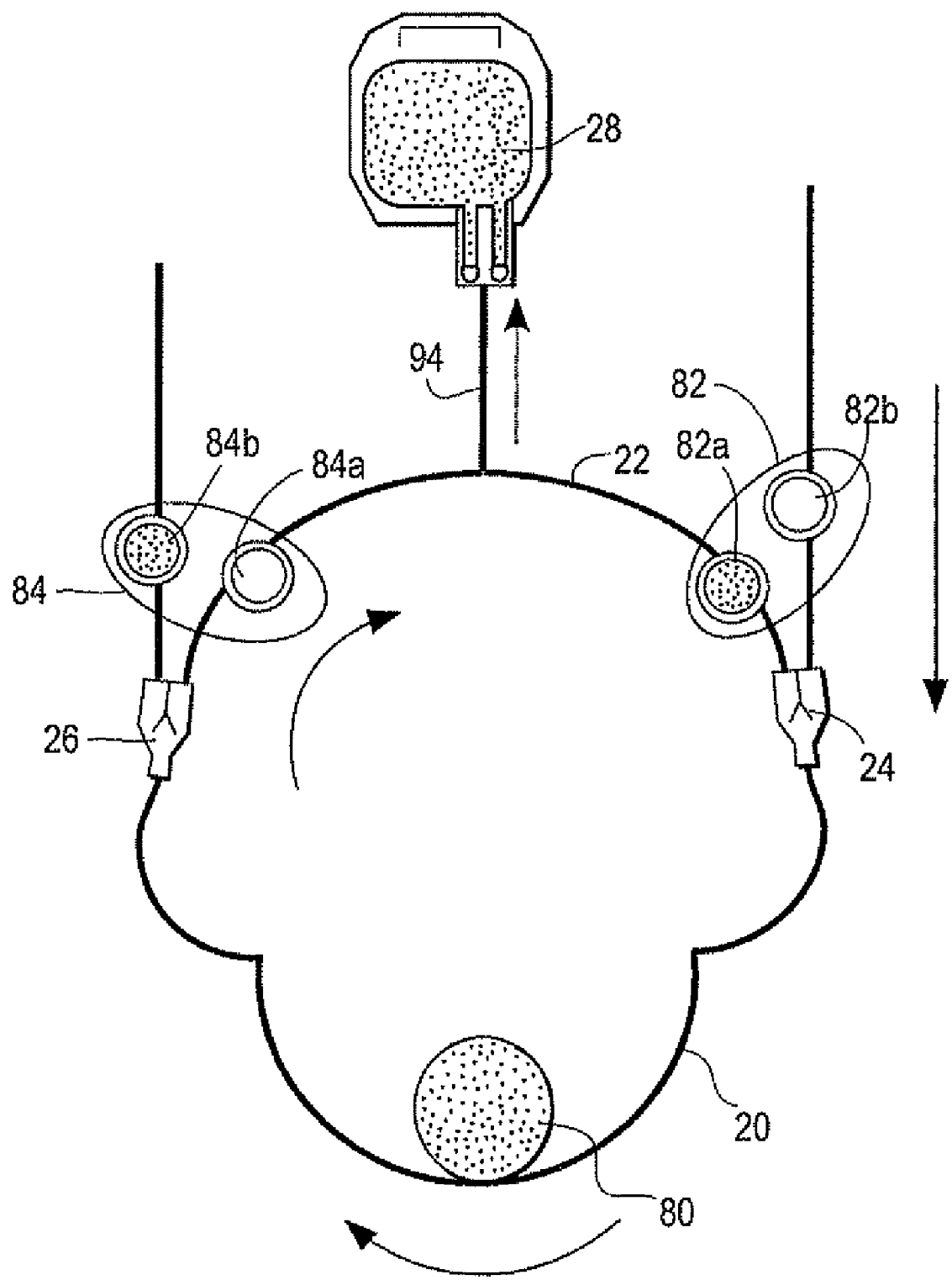
FIG. 4 is a diagrammatic view of a portion of the system of FIG. 3 in the draw cycle.

FIG. 3 illustrates the flow that occurs in a "draw" cycle using a single needle configuration, i.e., when blood is withdrawn from the blood source and returned to the blood source through the same needle or access device 70. As may be seen in FIG. 3, blood flows from the source, into and through the needle 70, into the portion of flow path 20 that is located distal of the flow communication site 30, and then is diverted at the flow communication site to flow into the first fluid flow path 18. This occurs by reason of selected closing and opening of the valves in valve array 54. Specifically, in the draw cycle, the valve 54 on the second or return flow path 20 is closed, so blood flow withdrawn through needle 70 cannot flow past the valve and is diverted at the flow communication site 30 into the inlet flow path 18. Valve 54 on the first inlet flow path 18 is in an open condition allowing flow therethrough. Further, the valve 54 on the saline flow path 48 is closed and the valve 54 on the anticoagulant flow path is open, allowing anticoagulant to be added to the blood withdrawn from the blood source at the anticoagulant access site or junction 40. Anticoagulated blood flows through the first or inlet flow path 18, and is metered by pump 56 into the inlet 14 of the blood processor 12. Blood components removed from the blood for storage, discarding and/or later use, exit through outlet 58, through flow path 60 and into container 62. Blood components separated by the processor and to be returned to the blood source exit from the processor through the outlet 16 into the blood return flow path 20. These blood components pass through open valve 82b (valve 82a being closed) under the force and control of pump 80 and through open valve 84a (valve 84b being closed), and into the reservoir, e.g., blood bag, 28. The reservoir allows the separated blood components to be temporarily stored for later return to the blood source during the return cycle.

Figure 5:
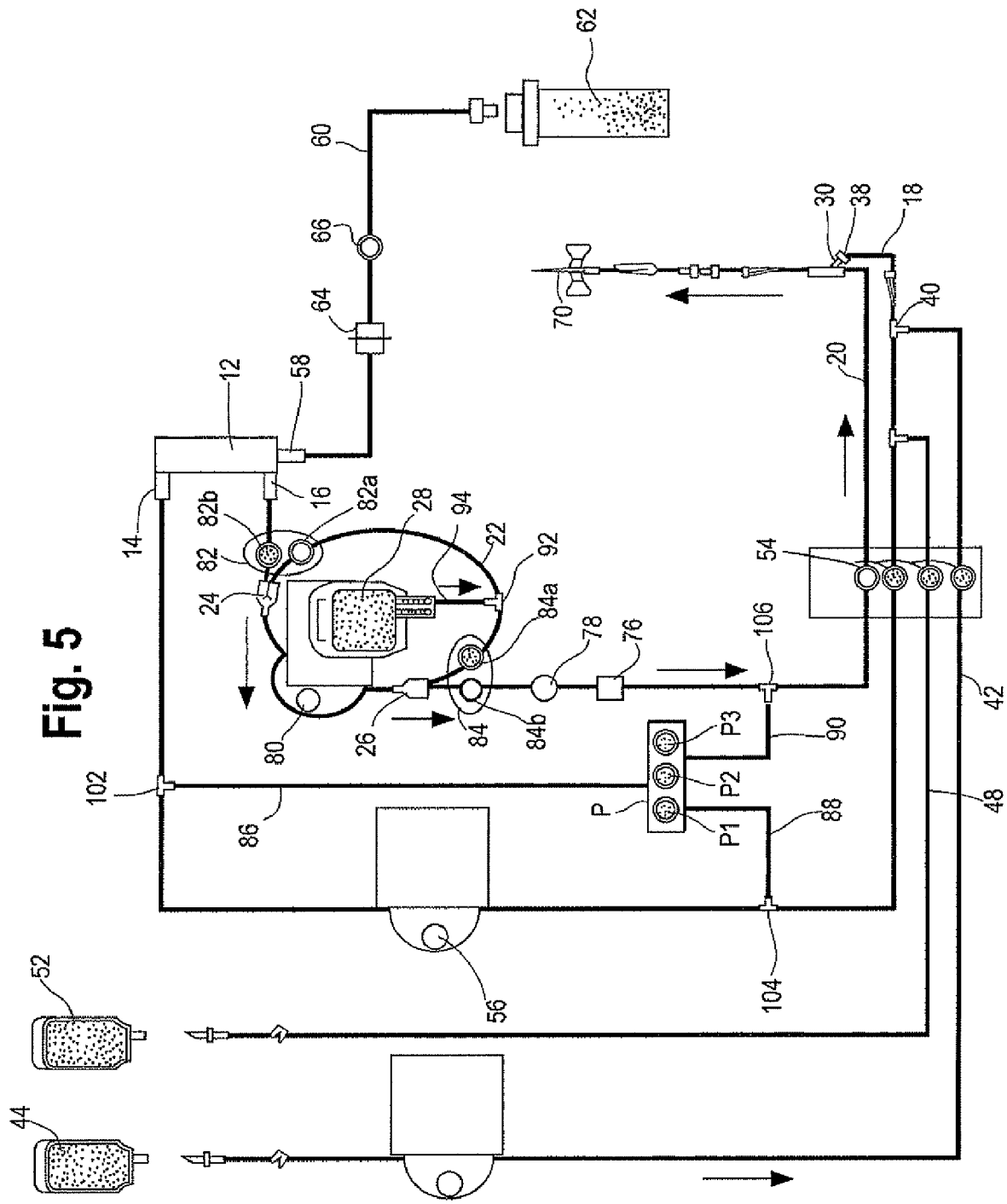
FIG. 5 is a diagrammatic view of the tubing system of FIG. 2 showing flow through the system in a return cycle.
Figure 6:
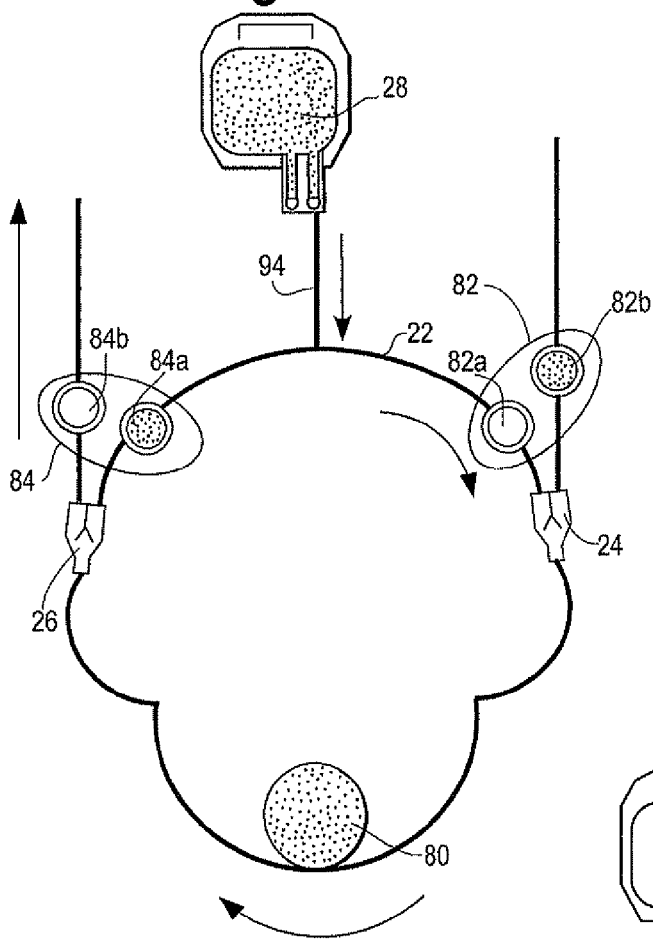
FIG. 6 is a diagrammatic view of a portion of the system of FIG. 5 in the return cycle.

The flow through the single access system during the "return" cycle, when separated blood components are returned to the blood source is illustrated in FIG. 5. As shown there, the valves 54 on the first or inlet flow path 18, the saline flow path 48 and the anticoagulant flow path 42 are all closed. The valve 54 on the second or return flow path 20 is open. Also, valves 82a and 84b are open and valves 84a and 82b are closed. As a consequence, separated blood components previously temporarily stored in reservoir 28 flow out of the reservoir into tubing segment 22, through valve 82a, under the force and control of pump 80 and through valve 84b, continuing through the second or return flow path 20 to the access member or needle 70 and back into the donor, patient or other blood source.

It may therefore be seen that this system requires only two pumps (other than the anticoagulant pump 46), whether in the single or double access arrangement. Pump 56 controls the draw from the source or donor in both single and double access, and pump 80 controls the return flow in flow path 20 in both single and double needle, as well as the flow into and from the reservoir 28 during single needle procedures.

After the previously collected and temporarily stored blood components are returned to the source, the system can then be recycled to the "draw" configuration previously described, where blood or blood components are again withdrawn from the source and are processed by the processor. In the draw cycle, separated components for return to the source are temporarily stored in reservoir 28, while blood components for discarding, or storing for later use, or processing can be directed into the storage container 62.

Accordingly, it can be seen that the blood processing system described herein provides a structure, system and method by which a single processing system may conveniently be used, on the one hand, as a double needle or double access system, as shown in FIG. 1, or, on the other hand, readily reconfigured as a single needle system as illustrated in FIG. 2. Although the subject matter described herein has been described in connection with specific examples and embodiments, it is understood that the subject matter is not limited to the specific embodiments shown or described but may include other embodiments or structures in keeping with the scope of the appended claims.

What is claimed is:

1. A blood processing system adapted for single or double access draw and return comprising:
    a blood processor for separating blood into one or more components, the blood processor including an inlet for receiving blood from a blood source and an outlet for returning at least one blood component to the source;
    a first flow path in communication with said inlet;
    a second flow path in communication with said outlet;
    a third flow path in communication with the second flow path at two spaced-apart locations;
    a reservoir in fluid communication with the third flow path between the two space-apart locations;
    a flow communication site associated with the second flow path downstream of the spaced-apart locations, which communication site is configured to permit communication with the first flow path.

2. A blood processing system in accordance with claim 1 in which the first flow path communicates with a first access device for accessing blood from a blood source and the second flow path communicates with a second access device for returning at least one blood component to a blood source.

3. A blood processing system in accordance with claim 1 comprising a valving system disposed to control flow through the first and second paths.

4. A blood processing system in accordance with claim 1 further comprising a first valve arrangement to control flow through one of the two spaced apart locations and a second valve arrangement to control flow through the other of the two spaced apart locations.

5. A blood processing system in accordance with claim 1 wherein the blood processor includes a second outlet for at least one blood component that is not being returned to the source and the system includes a collection flow path communicating with the second outlet.

6. A blood processing system in accordance with claim 5 further comprising a collection container communicating with said collection flow path.

7. A blood processing system in accordance with claim 1 further comprising a bypass flow path communicating between the second flow path and the first flow path.

8. A blood processing system in accordance with claim 7 further comprising a pump associated with the first flow path, and wherein the bypass flow path communicates with the first flow path upstream of the pump, and includes a flow branch communicating with the first flow path downstream of the pump.

9. In a blood processing system for alternating draw and return comprising a blood processor for separating blood into one or more components, the blood processor including an inlet for receiving blood from a blood source and an outlet for at least one blood component; a first flow path in communication with said inlet; and a second flow path in communication with said outlet;

the improvement comprising, in combination:
a flow path loop fluidly communicating with the second flow path; a reservoir in fluid communication with the flow path loop; and a valve arrangement associated with the flow path loop configured to control flow between the second flow path and the flow path loop so as to alternately direct flow fluid from the second flow path into the flow path loop and from the flow path loop into the second flow path.

10. A blood processing system in accordance with claim 9 further comprising a pump associated with the second flow path for directing fluid flow into and from the flow path loop.

11. A blood processing system in accordance with claim 10 wherein the flow path loop communicates with the second flow path upstream and downstream of the pump.

12. A blood processing system in accordance with claim 9 wherein the first flow path is adapted to communicate with a first access member and the second flow path is adapted to communicate with a second separate access member.

13. A blood processing system in accordance with claim 12 wherein the first and second flow paths may be optionally joined in fluid communication such that fluid flow through the first and second flow paths passes through only one of the access members.

14. A blood processing system in accordance with claim 9 further comprising a bypass flow path communicating between the first and second flow paths.

15. A blood processing system in accordance with claim 9 further comprising a third flow path communicating with the blood processor for removing at least one blood component.

16. A blood processing system in accordance with claim 9 wherein the flow path loop communicates with the second flow path at spaced apart locations, the system further comprising a pump associated with the second flow path between the spaced apart locations, and the valve arrangement adapted to operate in a first mode to alternately direct flow from the second flow path into the flow path loop at one of the spaced apart locations and from out of the flow path loop at the other of the spaced apart locations and a second mode such that fluid in the second flow path does not flow into or from the flow path loop.

17. A blood processing system in accordance with claim 9 further comprising a first fluid additive flow path communicating with the first flow path and a second fluid additive flow path communicating with the first fluid flow path.

18. A blood processing system in accordance with claim 17 comprising a valve array for selectively controlling flow through the first fluid flow path, second fluid flow path, first additive flow path, and second additive flow path.

* * * * *